United States Patent
Ogasawara et al.

(10) Patent No.: US 8,858,749 B2
(45) Date of Patent: Oct. 14, 2014

(54) METHOD AND APPARATUS FOR MAKING DISPOSABLE DIAPER

(75) Inventors: Yoshikazu Ogasawara, Kagawa (JP); Akira Hamada, Kagawa (JP)

(73) Assignee: Unicharm Corporation, Ehime (JP)

( * ) Notice: Subject to any disclaimer, the term of this patent is extended or adjusted under 35 U.S.C. 154(b) by 436 days.

(21) Appl. No.: 13/382,983

(22) PCT Filed: Jul. 8, 2010

(86) PCT No.: PCT/JP2010/004457
§ 371 (c)(1),
(2), (4) Date: Jan. 9, 2012

(87) PCT Pub. No.: WO2011/004605
PCT Pub. Date: Jan. 13, 2011

(65) Prior Publication Data
US 2012/0111485 A1  May 10, 2012

(30) Foreign Application Priority Data
Jul. 8, 2009 (JP) .................... 2009-162254

(51) Int. Cl.
*A61F 13/15* (2006.01)

(52) U.S. Cl.
CPC ..... *A61F 13/15609* (2013.01); *A61F 13/15699* (2013.01)
USPC .................... 156/177; 16/179; 16/440

(58) Field of Classification Search
None
See application file for complete search history.

(56) References Cited

U.S. PATENT DOCUMENTS

| | | | |
|---|---|---|---|
| 5,660,664 A * | 8/1997 | Herrmann ............. | 156/161 |
| 5,745,922 A * | 5/1998 | Rajala et al. ............. | 2/243.1 |
| 2007/0296104 A1* | 12/2007 | Shannon et al. .......... | 264/46.3 |

FOREIGN PATENT DOCUMENTS

| | | |
|---|---|---|
| EP | 1 563 817 A1 | 8/2005 |
| JP | 06-070958 A | 3/1994 |

(Continued)

OTHER PUBLICATIONS

Supplementary European Search Report from corresponding European application No. 10796916.4 dated Jun. 14, 2013 (7 pgs).

(Continued)

*Primary Examiner* — Barbara J Musser
(74) *Attorney, Agent, or Firm* — Brinks Gilson & Lione

(57) ABSTRACT

The present invention aims to provide method and apparatus for making a disposable diaper improved so that a region of the continuous elastic predetermined to extend across the middle of the crotch region may be attached to continuous web in a desired condition. A method for making a disposable diaper 10 includes the steps of, (A) coating a first surface 102A of a first web 102 with an adhesive 130 to define an adhesion region 131 extending from first side edge 106 toward second side edge 107 in a cross direction CD and a non-adhesion region 134 extending along the second side edge 107 in a machine direction MD; (B) rocking the continuous elastic 104 by a rocker arm 113 in the cross direction CD and thereby laying the continuous elastic 104 on the first surface 102A of the first web 102 in a curved pattern such that the continuous elastic 104 may have crest-segments 104*a* each curving convexly toward the first side edge 106, trough-segments 104*b* each defined between a pair of the adjacent crest-segments 104*a* and curving concavely from the first side edge 106 and intermediate segments 104*c* connecting the crest-segments 104*a* to the trough-segments 104*b*; (C) attaching the continuous elastic 104 including the trough-segments 104*b* and the intermediate segments 104*c* but except the trough-segments 104*b* to the first surface 102A of the first web 102 in the adhesion regions 131 by a first pressure roll 112; and (D) putting flat and bonding together the first web 102 and the second web 105 by a second pressure roll 118.

4 Claims, 9 Drawing Sheets

(56) References Cited

FOREIGN PATENT DOCUMENTS

| JP | 06-311999 A | 11/1994 |
| JP | 2001-087314 A | 4/2001 |
| JP | 2006-141642 | 6/2006 |
| JP | 2006-141642 A | 6/2006 |
| JP | 2009-090029 A | 4/2009 |

OTHER PUBLICATIONS

International Search Report from corresponding PCT application No. PCT/JP2010/004457 dated Oct. 5, 2010 (1 pg).

* cited by examiner

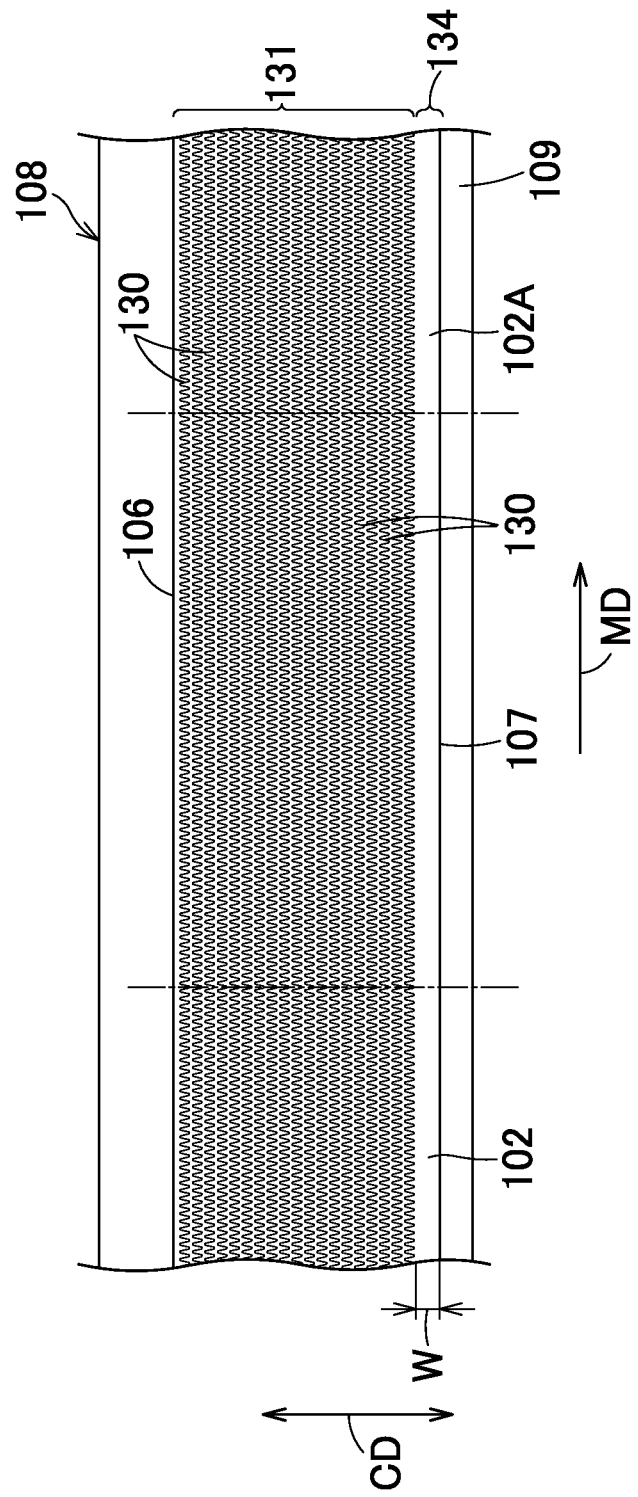

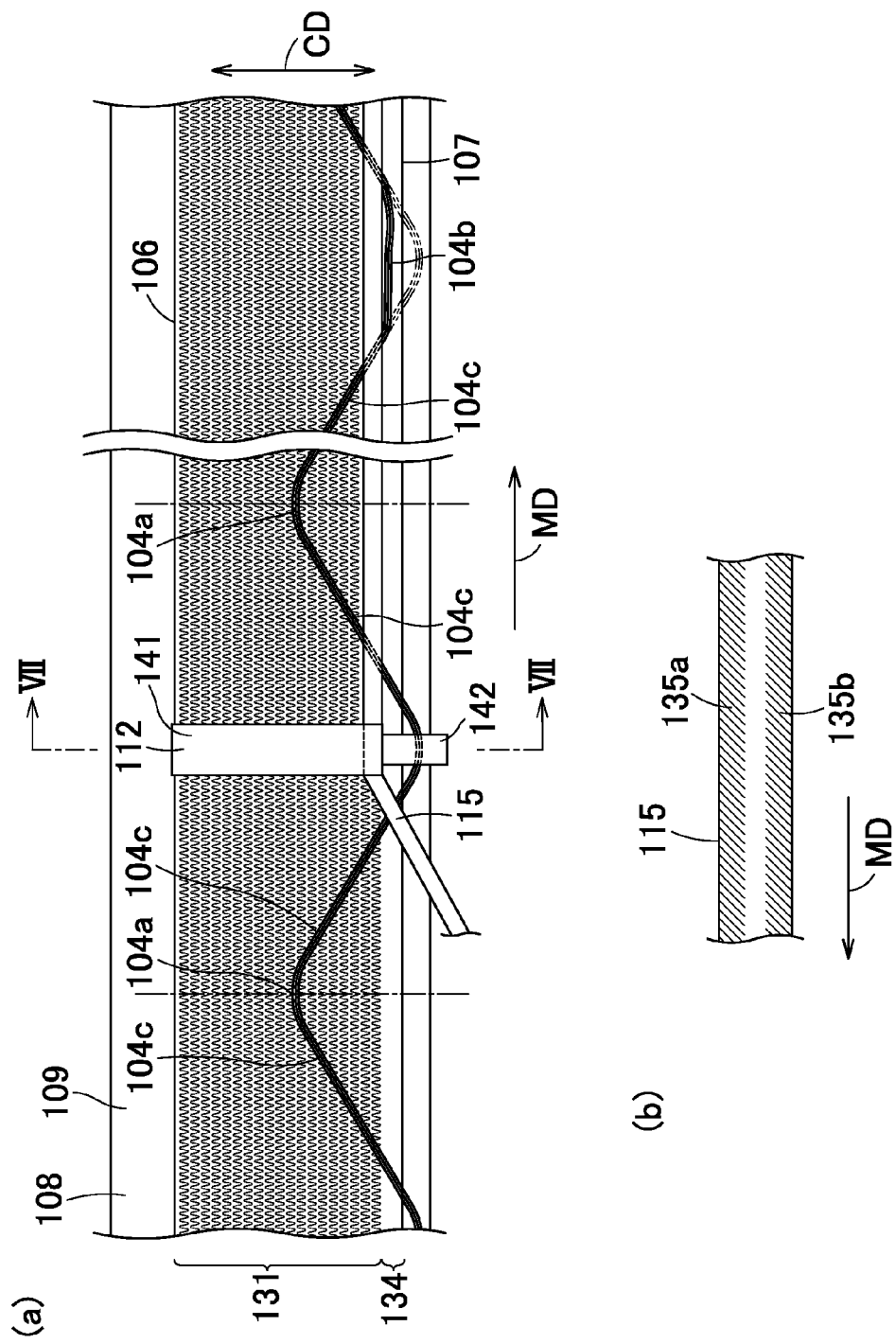

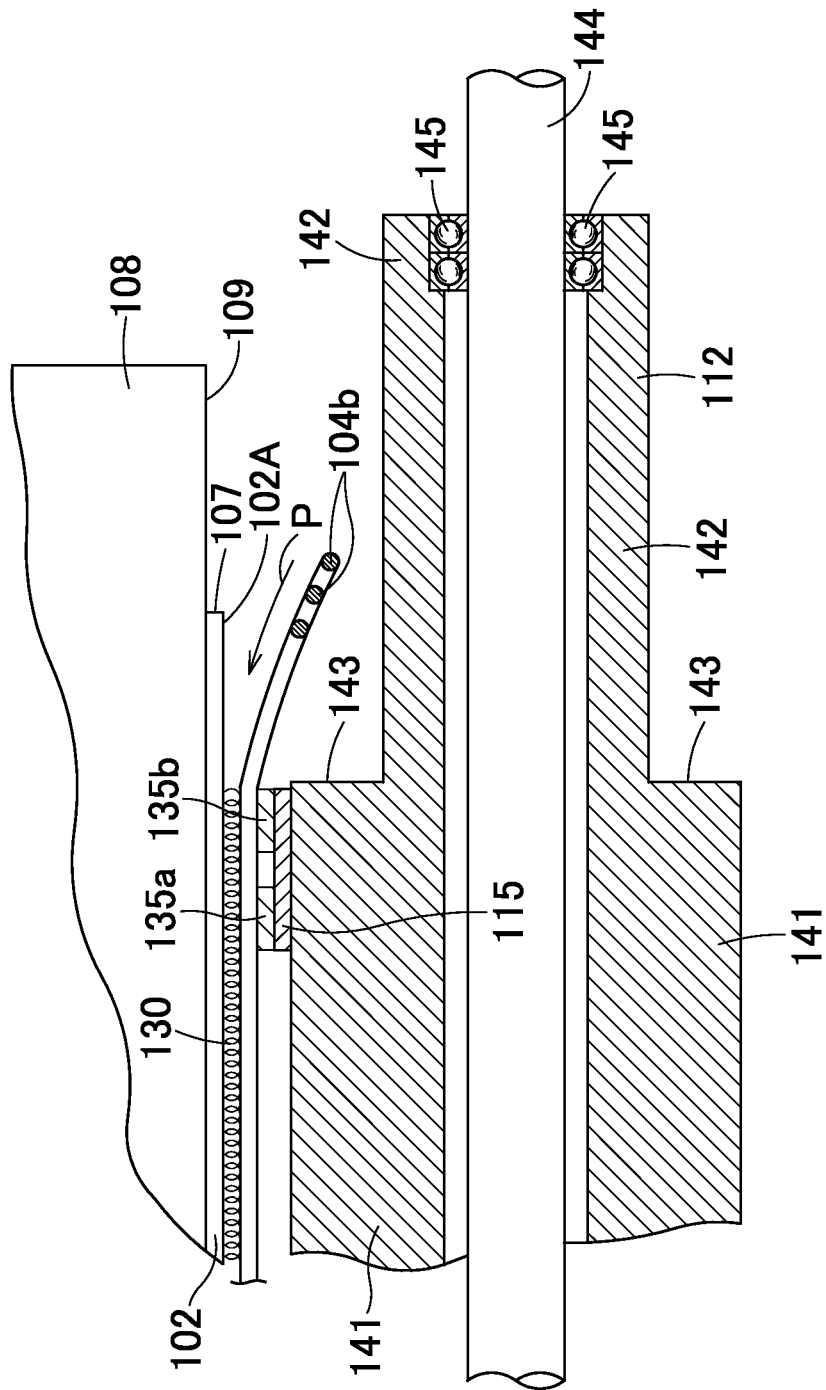

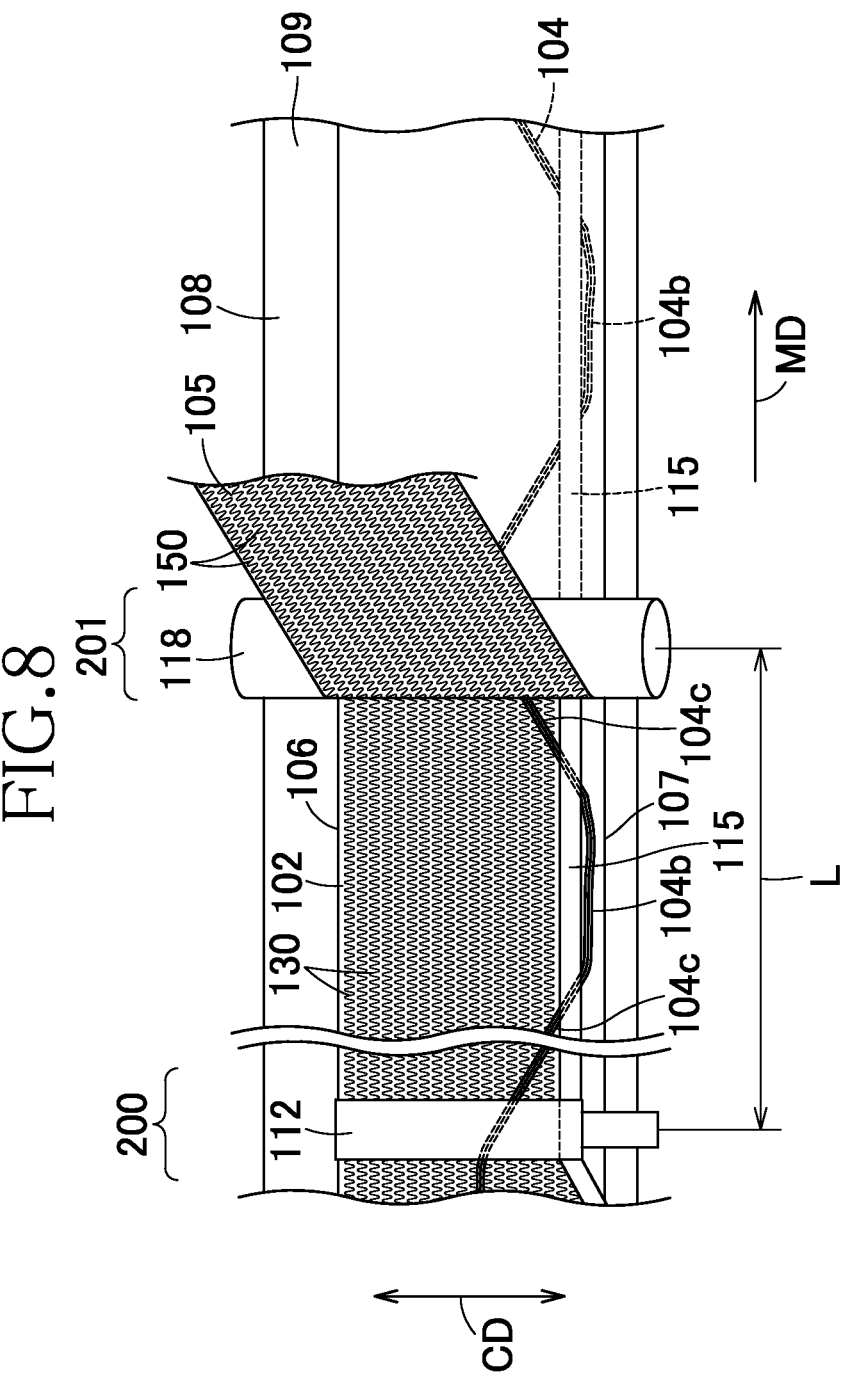

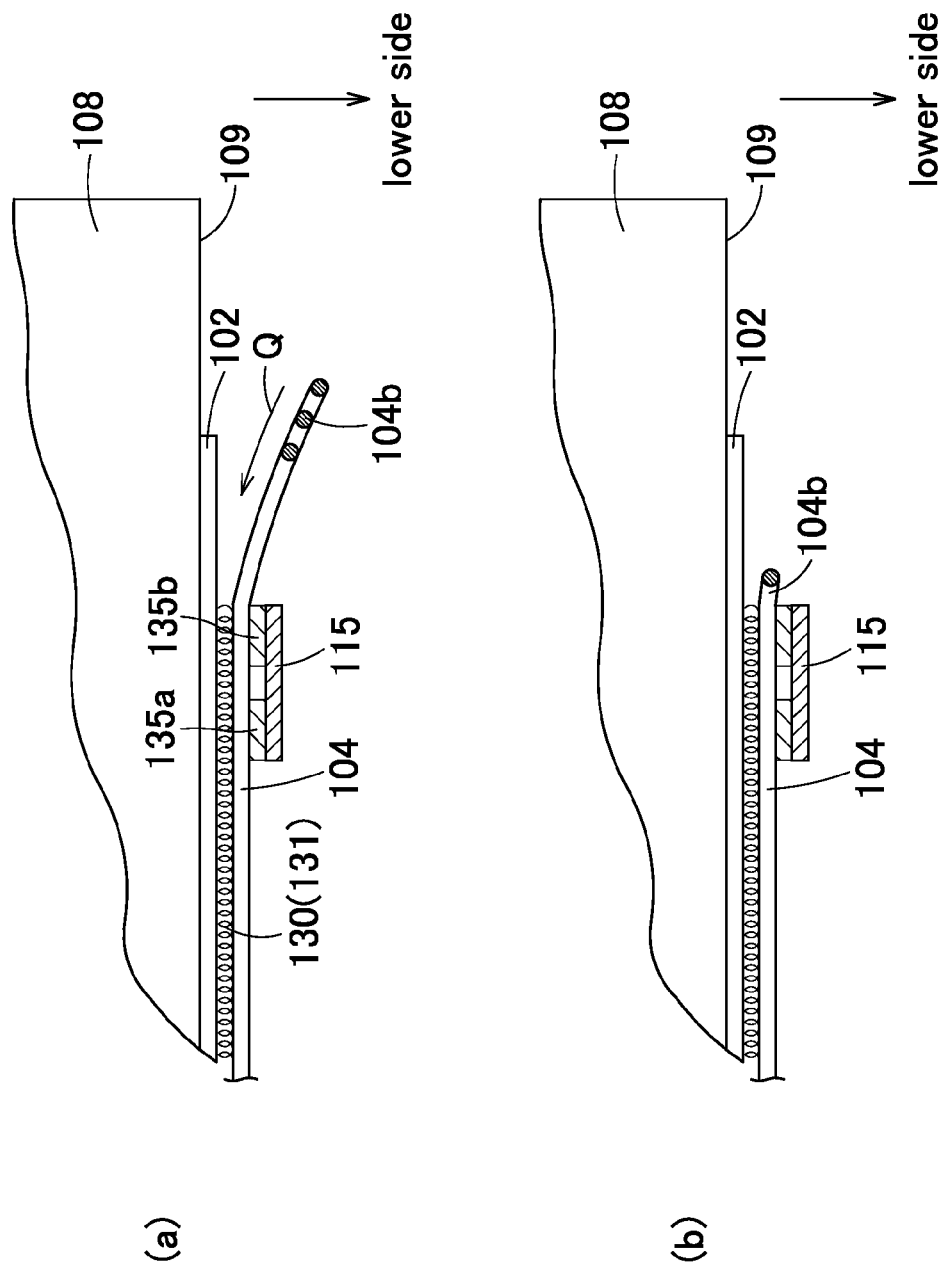

METHOD AND APPARATUS FOR MAKING DISPOSABLE DIAPER

RELATED APPLICATION

This application is a 35 U.S.C. §371 national phase filing of International Patent Application No. PCT/JP2010/004457, filed Jul. 8, 2010, through which and to which priority is claimed under 35 U.S.C. §119 to Japanese Patent Application No. 2009-162254, filed Jul. 8, 2009.

TECHNICAL FIELD

The present invention relates to a method of making a disposable diaper provided with an elastic extending from a peripheral edge of one leg-opening across a crotch region to a peripheral edge of the other leg-opening and relates also to an apparatus used to put the method in practice.

RELATED ART

In the continuous production process of disposable diapers, it is well known to supply to a continuous web running in a machine direction with a continuous elastic being oscillated in a cross direction with respect to the machine direction and to attach the continuous elastic under tension to the continuous web. For example, JP 2006-141642 A discloses a method for making a composite web comprising first and second webs each in the form of a continuous fibrous nonwoven fabric and first and second continuous elastics both fixedly sandwiched between the first and second webs to curve.

In the production process of disposable diapers, in general, the region of a continuous elastic to be placed on a continuous web in a wavy pattern which should extend across the middle of the crotch region is desired to be provided not under tension on a substantially rectilinear position parallel to the machine direction or cut.

To embody such desired condition, JP 2006-141642 A discloses a method for making a diaper. According to the method disclosed in JP 2006-141642 A, first and second continuous elastics are attached in a curved pattern to respective inner surfaces of a first web and a second web by adhesive immediately before these two webs are squeezed between the nip rolls. However, in such a case, since these continuous elastics are sandwiched between the first web and the second web before the region adapted to extend across the middle of the crotch region contracts to be rectilinear, even though the region is not bonded to the webs by adhesive, it is difficult for the region sandwiched between these two webs to be rectilinear.

CITATION LIST

Patent Literature

[PLT 1] JP 2006-141642 A

SUMMARY

A disposal diaper which can be made by a method and an apparatus in accordance with one or more embodiment of the present invention comprises a composite web including a first web, a second web laminated with and bonded to the first web and a continuous elastic sandwiched and bonded between the first web and the second web to curve, wherein the first web has a first surface, a second surface opposed to the first surface, a first side edge extending in a machine direction and a second side edge opposed to and spaced from the first side edge in a cross direction orthogonal to the machine direction.

A first aspect of the present invention is a method comprising the steps of: (A) coating the first surface of the first web with an adhesive to define an adhesion region extending from the first side edge toward the second side edge in the cross direction and a non-adhesion region extending along the second side edge in the machine direction; (B) rocking the continuous elastic by a rocker arm in the cross direction and thereby laying the continuous elastic on the first surface of the first web in a curved pattern such that the continuous elastic has crest-segments each curving convexly toward the first side edge, trough-segments each defined between a pair of adjacent the crest-segments and curving concavely from the first side edge and intermediate segments connecting the crest-segments to the trough-segments; (C) attaching the continuous elastic including the trough-segments and the intermediate segments but except the trough-segments to the first surface of the first web in the adhesion region by a first pressure roll; and (D) putting flat and bonding together the first web and the second web by a second pressure roll.

A second aspect of the present invention is an apparatus being characterized in that: the apparatus includes at least a rotary drum adapted to carry out a step of attaching the continuous elastic to the first web and a pressure roll provided in face-to-face relationship with the rotary drum; the continuous elastic has segments attached to the first surface of the first web in an adhesion region coated with an adhesive and segments left free in a non-adhesion region of the first surface of the first web coated with no adhesive; the pressure roll has a cylindrical shape having a smaller-diameter section on a side of one end in comparison to a section on a side of an other end and adapted to be not responsible for a press step; and the smaller-diameter section is kept spaced from and opposed to the regions of the continuous elastic lying in the non-adhesion region in a step during which the first web having the continuous elastic placed thereon is squeezed between the rotary drum and the pressure roll.

BRIEF DESCRIPTION OF DRAWINGS

FIG. 5 is a plan view illustrating a step (A).

FIG. 6(a) is a plan view illustrating a step of traversing and FIG. 6(b) is a partially scale-enlarged view showing details of adhesive line.

FIG. 7 is a diagram illustrating a first press step partially in plan view.

FIG. 8 is a diagram illustrating a second press step partially in plan view.

FIGS. 9(a) and 9(b) are diagrams illustrating how trough-segments of the continuous elastic behave in the course of running along a distance L.

DETAILED DESCRIPTION

Figure 1:
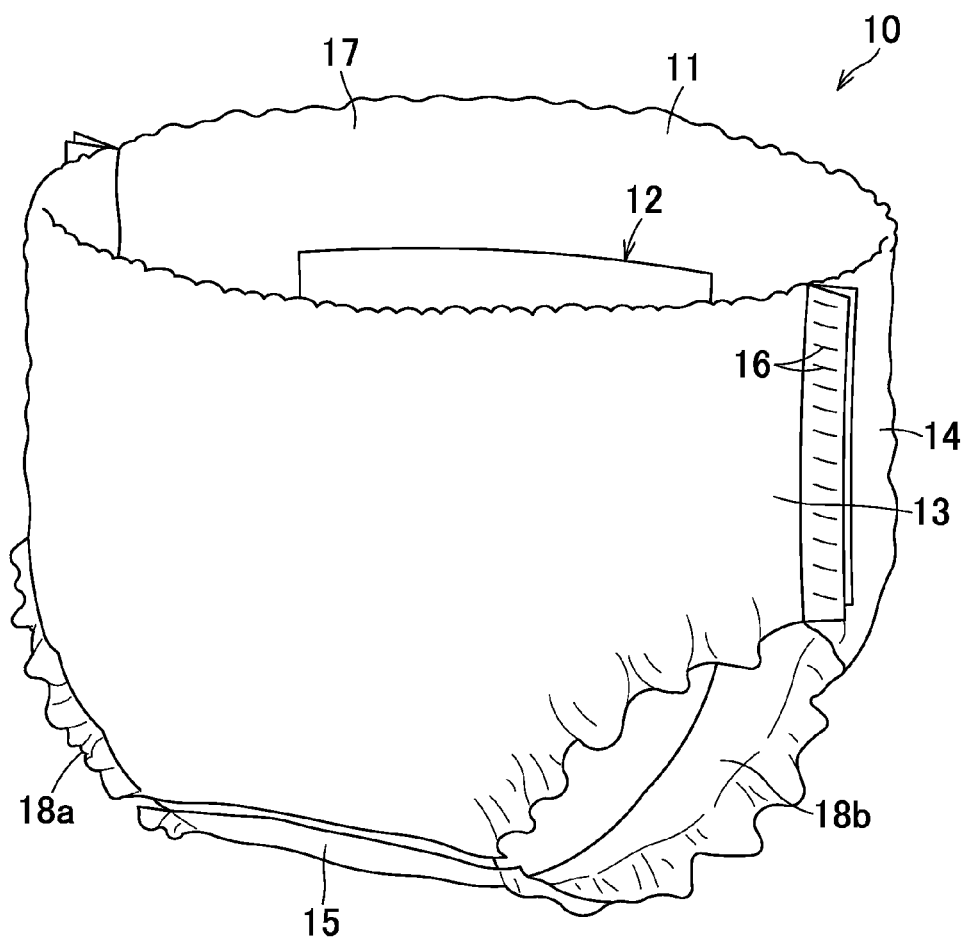
FIG. 1 is a perspective view of a diaper made by using the method according to one or more embodiment of the present invention.
Figure 2:
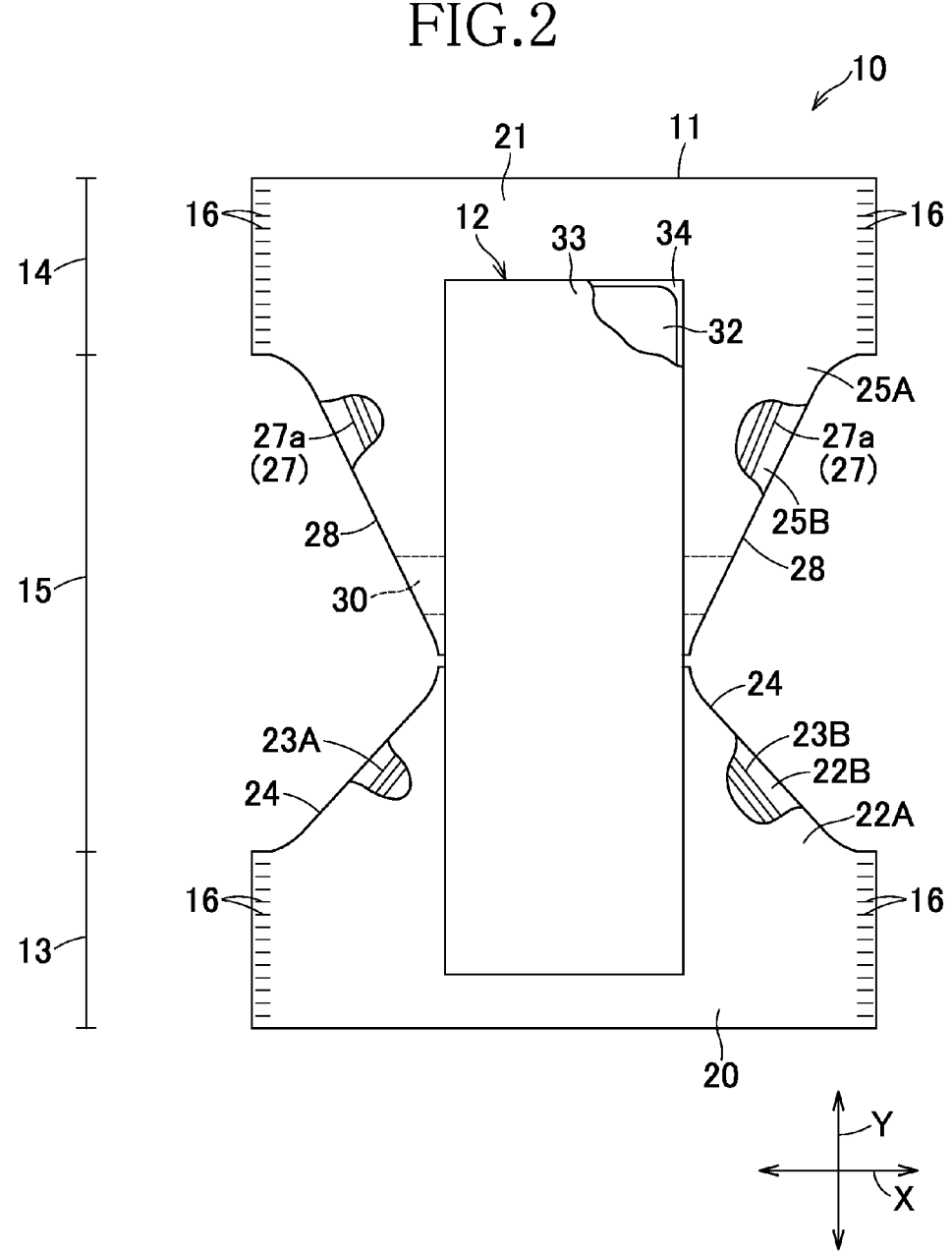
FIG. 2 is a partially cutaway plan view of the diaper as flatly developed.
Figure 3:
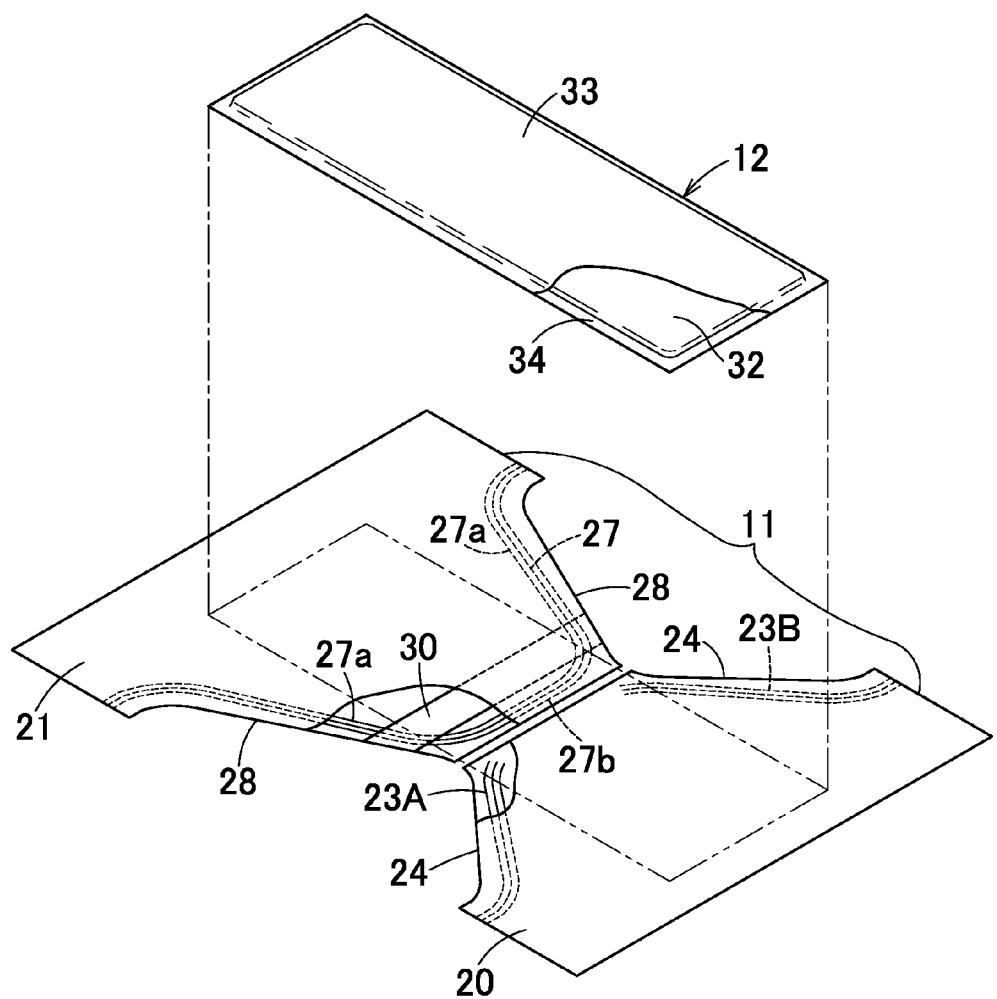
FIG. 3 is a partially exploded perspective view of the diaper.

FIG. 1 is a perspective view of a disposable diaper 10 obtained by a method according to one or more embodiment of the present invention, FIG. 2 is a partially cutaway plan view of the disposable diaper 10 as flatly developed and FIG. 3 is an exploded perspective view of the disposable diaper 10 showing an outer member 11 and a liquid-absorbent structure 12 as set apart from each other.

The disposable diaper 10 has a longitudinal direction Y, a transverse direction X orthogonal to the longitudinal direction Y, a skin-facing side and a non-skin-facing side and comprising an outer member 11 defining a pant-like outer shape, a liquid-absorbent structure 12 attached to an inner surface of the outer member 11, a front waist region 13, a rear waist region 14 and a crotch region 15 extending between these two waist regions 13, 14. A liquid-absorbent structure 12 is attached to the inner surface of the outer member 11 to extend across the crotch region 15 further into the front and rear waist regions 13, 14.

Of the outer member 11, the front and rear waist regions 13, 14 are put flat and joined together along respective transversely opposite side edges using an appropriate technique selected from various known thermal bonding techniques such as heat seal, supersonic seal or hot embossing, whereupon a waist-opening 17 and a pair of leg-openings 18a, 18b are defined.

The outer member 11 comprises a front section 20 and a rear section 21 wherein the front section 20 is defined by the front waist region 3 and a part of the crotch region 15 and the rear section 21 is defined by the rear waist region 14 and the rest of the crotch region 15.

The front section 20 comprises a inner sheet 22A lying on the skin-facing side, an outer sheet 22B lying on the non-skin-facing side and elastics 23A, 23B each comprising a plurality of elastic strands and sandwiched between the inner and outer sheets 22A, 22B associated with front half peripheral edges of the respective leg-openings 18a, 18b. The elastics 23A, 23B are attached to the inner surface (s) of the inner sheet 22A and/or the outer sheet 22B by hot melt adhesive along the front half peripheral edges of the respective leg-openings 18a, 18b to curve, respectively.

The rear section 21 comprises a inner sheet 25A lying on the skin-facing side, an outer sheet 25B lying on the non-skin-facing side and an elastic 27 comprising a plurality of elastic strands associated with rear half peripheral edges of the respective leg-openings 18a, 18b sandwiched between the inner and outer sheets 25A, 25B. The elastic 27 is attached to the inner surface(s) of the inner sheet 25A and/or the outer sheet 25B by hot melt adhesive along the rear half peripheral edges of the respective leg-openings 18a, 18b.

The elastic 27 associated with rear half peripheral edges of the respective leg-openings 18a, 18b describe, as a whole, a pattern which is convex from the rear waist region 14 toward the crotch region 15 and comprise transversely opposite side edge segments 27a, 27a curving along the rear half peripheral edges 28 of the respective leg-openings 18a, 18b and middle segments 27b extending across the middle of the crotch region in a transverse direction to define a substantially rectilinear segment.

The rear section 21 includes a relatively narrow auxiliary sheet 30 extending in the transverse direction X. The auxiliary sheet 30 is sandwiched between the inner and outer sheets 25A, 25B and fixed therebetween by hot melt adhesive (not shown). As will be described later in more details, the auxiliary sheet 30 is provided in order to prevent the middle segments 27b of the elastic 27 from being displaced toward the front waist region 13 in the course of the production process of the diaper 10.

The liquid-absorbent structure 12 has a rectangular shape which is relatively long in the longitudinal direction Y and comprises a bodily fluid-absorbent core assembly 32, a liquid-pervious top-sheet 33 lying on the skin-facing side of the bodily fluid-absorbent core assembly 32 and a liquid-impervious back-sheet 34 lying on the non-skin-facing side of the bodily fluid-absorbent core assembly 32. More specifically, the bodily fluid-absorbent core assembly 32 comprises a liquid-absorbent core formed from mixture of fluff pulp and super-absorbent polymer particles wrapped as a whole with a tissue paper. Both the top-sheet 33 and the back-sheet 34 extend outward beyond an outer peripheral edge of the bodily fluid-absorbent core assembly 32 and put flat and bonded together outside the outer peripheral edge of the bodily fluid-absorbent core assembly 32 by hot melt adhesive (not shown).

Figure 4:
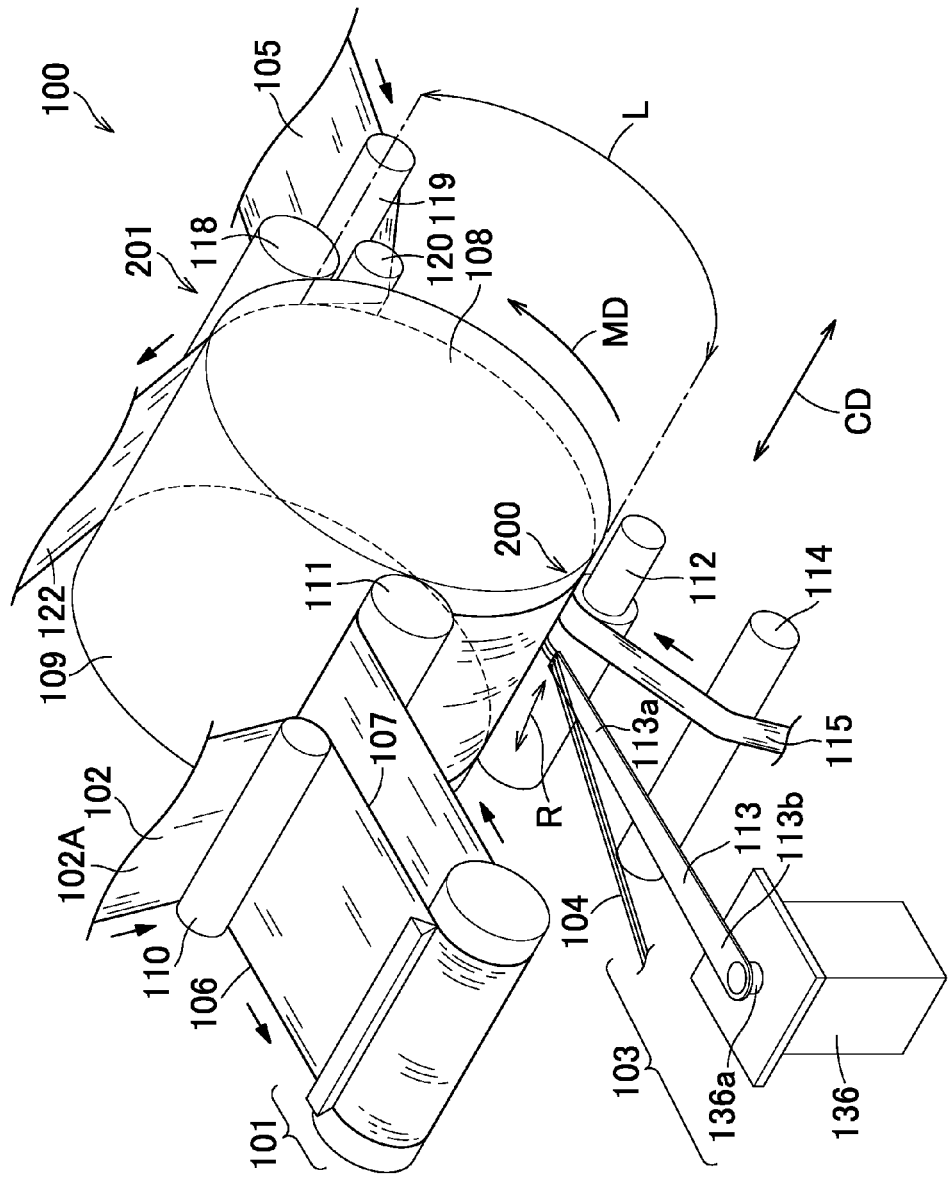
FIG. 4 is a schematic diagram partially illustrating an apparatus for making the diaper.

FIG. 4 is a schematic diagram partially illustrating an apparatus 100 for making the diaper 10, FIG. 5 is a partial plan view illustrating a step (A) 101 carried out in the apparatus 100 to coat a first web 102 with hot melt adhesive in a predetermined pattern, FIG. 6(a) is a plan view illustrating a step (B) 103 to place continuous elastic 104 on first web 102 using a traverse mechanism 103 and FIG. 6(b) is a partially scale-enlarged view of a continuous auxiliary sheet 115, showing details of adhesive lines 135a, 135b coated on this continuous auxiliary sheet 115.

FIG. 4 illustrates a step of making the rear section 21 of the outer member 11 in the diaper production process. In this step, the first web 102 as material for the outer sheet 25B is fed onto an outer peripheral surface 109 of a rotary drum 108 located in an assembly station and held in close contact with the outer peripheral surface 109 under the effect of a suction mechanism (not shown) of known art. Then continuous elastic 104 as a material for the elastic elements 27 associated with rear half peripheral edges of the respective leg-openings 18a, 18b is attached to the first web 102 and a second web 105 as a material for the inner sheet 25A. In the accompanying drawings including FIG. 4, the machine direction in which the first web 102 is fed is designated by MD and the cross direction orthogonal to this machine direction MD is designated by CD. It should be also understood that a longitudinal direction of the first web 102 (machine direction MD) corresponds to the transverse direction X of the diaper 10 and a width direction (cross direction CD) of the first web 102 corresponds to the longitudinal direction Y of the diaper 10.

The first web 102 has a first surface 102A, a second surface opposite to the first surface 102A, a first side edge 106 extending in the machine direction MD and a second side edge 107 opposite to and spaced from the first side edge 106 in the cross direction CD. The first web 102 delivered from a feed roll (not shown) is stretched by a stretcher roll (not shown) in the cross direction CD and fed in such a stretched state in the machine direction MD. Then the first web 102 is turned around by a guide roll 110 to be guided to an adhesive coating mechanism 101 adapted to coat the first surface 102A with the hot melt adhesive in the step (A).

Now the first web 102 is turned around by a guide roll 111 to be fed into a nip defined between the rotary drum 108 and a first pressure roll 112 facing the rotary drum 108. The continuous elastic 104 is rocked in the cross direction CD by a rocker arm 113 of the traverse mechanism 103 in the step (B) in the course of being attached to the first surface 102A and squeezed together with the continuous auxiliary sheet 115 guided by a guide roll 114 between the first pressure roll and the rotary drum 108 in the step (C). The first web 102 to which the continuous elastic 104 and the continuous auxiliary sheet 115 have been attached in this manner is further fed in the machine direction MD into a nip defined between the rotary drum 108 and a second pressure roll 118 facing the rotary drum 108 in a lower, i.e., downstream region of the rotary drum 108 at a distance L from the first pressure roll 112. The second web 105 stretched in the cross direction CD by a stretcher roll 119 is guided by a guide roll 120 to be fed into a nip defined between the second pressure roll 118 and the rotary drum 108 and squeezed together with the first web 102 by the second pressure roll 118 and the rotary drum 108 in the step (D). In this way, these two webs 102, 105 are bonded together to form a composite web 122 which is further fed downstream.

Details of the step (A) 101, the step (B) 103, the step (C) 200 and the step (D) 201 will be described below in this order.

<Step (A)>

Referring to FIGS. 4 and 5, in the step (A) 101, the first surface 102A of the first web 102 is coated with hot melt adhesive 130 in a wavy pattern to define an adhesion region 131 extending from the first side edge 106 toward the second side edge 107 in the cross direction CD and a non-bonded region 134 defined between the adhesion region 131 and the second side edge 107 and extending in the machine direction MD. While the width dimension W of the non-bonded region 134 in the cross direction CD may be appropriately selected depending on factors such as a size of the diaper 10 as a whole to be made, this width dimension is preferably in a range of about 10 to about 20 mm. This is for the reason that the first web 102 may be sometimes slightly displaced in the cross direction CD as it is fed in the machine direction MD in the course of production process and the width dimension of 10 mm or less may result in the final product having the continuous elastic 104 exposed outward from the first web 102.

While the adhesion region 131 is defined by the hot melt adhesive 130 coated in the wavy pattern in the illustrated embodiment, it is possible without departing from the scope of the invention to coat the hot melt adhesive 130 in various patterns of known art such as a sprayed pattern, a spiral pattern or a dotted pattern.

Referring to FIG. 4, the first web 102 coated with the hot melt adhesive 130 is turned about by the guide roll 111 to be fed toward the outer peripheral surface 109 of the rotary drum 108.

<Step (B)>

The continuous elastic 104 is fed to the traverse mechanism 103 as it is stretched at a predetermined ratio by a stretcher roll (not shown). The continuous elastic 104 comprises three of preferably flat elastic strands. It should be appreciated here that various factors of the continuous elastic 104 such as the shape, the stretching ratio and the number of elastic strands may be appropriately selected depending on the tensile force requirement.

As will be apparent from FIG. 4, the rocker arm 113 comprises a distal end 113a provided with means (not shown) adapted to hold and guide the elastic inserted therethrough and a proximal end 113b opposite to the distal end 113a and directly fixed to a rocking shaft 136a of a control mechanism 136 including a servo-motor or the like. Rocking direction (designated by double-headed arrow R), velocity and rocking range of the rocker arm 113 are controlled by the control mechanism 136 so that the rocker arm 113 may rock at a desired high velocity. The rocker arm 113 extends substantially at right angle to the first web 102 running on the rotary drum 108.

Referring to FIGS. 4 and 6(a), the continuous elastic 104 is rocked at a predetermined velocity in the cross direction CD by the rocker arm 113 to describe on the first surface 102A of the first web 102 a wave-like curve repeating amplitude in the cross direction CD and attached to the first surface 102A of the first web 102 in this pattern. The continuous elastic 104 attached to the first surface 102A in this manner comprises bonded crest-segments 104a which are convex toward the first side edge 106, trough-segments 104b each defined between each pair of the adjacent crest-segments 104a to be concave with respect to the first side edge 106 and bonded intermediate segments 104c each connecting the crest-segment 104a with the trough-segment 104b. The trough-segments 104b extend outward beyond the second side edge 107 of the first web 102 on the outer peripheral surface 109 of the rotary drum 108 and are not bonded to the first surface 102A.

Specifically, the trough-segments 104b lie on the non-adhesion region 134 and/or on the outer peripheral surface 109 of the rotary drum 108 so that the trough-segments 104b are not fixed to the first surface 102A of the first web 102 and free therefrom. The tensile force of the continuous elastic 104 behaving to straighten the trough-segments 104b in parallel to the machine direction MD is exerted on the trough-segments 104b. Consequently, the trough-segments 104b are displaced from the initial position (indicated by chain double-dashed lines) on the first surface 102A of the first web 102 toward the middle of the first web 102 gradually over time. After a predetermined time period has elapsed, the trough-segments 104b are displaced to the position of the continuous auxiliary sheet 115 as indicated by a solid line. Taking this in consideration, even if the trough-segments 104b extend outward beyond the width of the product in the traverse step 103, it is unnecessary to provide the first web 102 sufficiently wide to support the trough-segments 104b. In other words, waste of material for the first web 102 can be reduced.

Referring again to FIG. 4, substantially at the same time the continuous elastic 104 with its crest- and intermediate segments is placed on and attached and bonded to the first surface 102A of the first web 102, the continuous auxiliary sheet 115 made of a fibrous non-woven fabric is turned around via a guide roll 114 to be fed into a nip between the first pressure roll 112 and the rotary drum 108.

The continuous auxiliary sheet 115 extends in the machine direction MD and has a relatively small width dimension, more specifically, in a range of about 20 to about 40 mm and intersects the intermediate segments 104c of the continuous elastic 104. Referring to FIG. 6(b), the surface of the continuous auxiliary sheet 115 facing the first surface 102A of the first web 102 is linearly coated with hot melt adhesive to form two adhesion lines 135a, 135b extending in the machine direction MD. The continuous auxiliary sheet 115 is squeezed between the first pressure roll 112 and the rotary drum 108 and thereby fixed to the bonded region 130 of the first web 102 by the adhesion lines 135a, 135b. In this way, the continuous auxiliary sheet 115 is fixed by dually coated adhesive, i.e., the adhesion region 131 and the adhesion lines 135a, 135b to the first web 102 and thereby the continuous auxiliary sheet 115 is stably fixed to the first surface 102A of the first web 102.

FIG. 7 is a sectional view taken along the line VII-VII in FIG. 6(a).

<Step (C)>

The first pressure roll 112 is substantially in the form of a cylinder extending in the cross direction CD and comprises a relatively large-diameter section 141 facing the first side edge 106 of the first web 102 and adapted to be responsible for the step (C) and a relatively small-diameter section 142 facing the second side edge 107 of the second web 105 and adapted to be not responsible for the step (C). A boundary between the large-diameter section 141 and the small-diameter section 142 is defined by a step 143. The first pressure roll 112 has a rotary shaft 144 extending through the interior thereof and supported by bearings 145.

In the step (C) 200, as will be apparent from FIG. 7, the trough-segments 104b of the continuous elastic 104 extends outside the step 143, i.e., in the non-adhesion region 134 and on the outer peripheral surface 109 of the rotary drum 108. The small-diameter section 142 of the first pressure roll 112 which is not responsible for the press step is spaced from the continuous elastic 104 as well as from the first surface 102A of the first web 102. Consequentially, the trough-segments 104b of the continuous elastic 104 is not pressed by the first pressure roll 112 against the first surface 102A of the first web 102 and the trough-segments 104b are maintained free from the first surface 102A.

The trough-segments 104b of the continuous elastic 104 are necessarily displaced inward under the contractile force to restore the initial rectilinear state parallel to the machine direction MD. However, such displacement is effectively restricted by the intermediate segments 104c fixed by the continuous auxiliary sheet 115 even if the contractile force exerted on the trough-segments 104b is relatively high. Eventually the trough-segments 104b are put in contact with the continuous auxiliary sheet 115 and thereby prevented from further moving toward the first side edge 106 beyond the continuous auxiliary sheet 115.

Since the hot melt adhesive 130 inevitably stick on the outer peripheral surface of the first pressure roll 112 in the step (C), the outer peripheral surface of the first pressure roll 112 may be covered with appropriate non-adhesive exchangeable member such as silicon rubber or pressure-sensitive adhesive tape.

FIG. 8 is a diagram illustrating a step of bonding the first web 102 and the second web 105 to each other to form composite web 122 un the Step (D), FIGS. 9(a) and (b) are diagrams illustrating the trough-segment 104b of the continuous elastic 104 hanging down under its own weight immediately before the first web 102 and the second web 105 are bonded to each other.

<Step (D)>

Referring to FIG. 8, after the continuous elastic 104 and the continuous auxiliary sheet 115 have been fixed to the first surface 102A of the first web 102 by the first pressure roll 112 cooperating with the rotary drum 108, in the lower region (See FIG. 3) of the rotary drum, the first web 102 is conveyed now in the machine direction MD. The surface of the second web 105 opposed to the first surface 102A of the first web 102 and coated with the hot melt adhesive 150. The first web 102 and this second web 105 are bonded together with the hot melt adhesive 150 as these two webs 102, 105 are squeezed between the second pressure roll 118 and the rotary drum 108.

In the production process according to the present invention, a distance L between a station to implement the step (C) and a station to implement the step (D) is set to be longer than distances between any other pairs of successive steps. This is for the purpose of assuring sufficient time before the trough-segments 104b left free restore the initial rectilinear positions. More specifically, if the first web 102 and the second web 105 are bonded to each other without waiting for elapse of the time required for the trough-segments 104b to restore the initial rectilinear positions, the trough-segments 104b still under tension would be sandwiched between these two webs 102, 105. In consequence, the trough-segments 104b still under tension would be attached to the crotch region 15 of the diaper 10. Contraction of the trough-segments 104b would cause undesirable deformation of the liquid-absorbent core assembly 35 and lead to a lowering in the absorption capacity. However, the method according to the present invention allows the trough-segments 104b to restore the initial rectilinear positions before the first web 102 and the second web 105 are bonded to each other so that the tensile force of the continuous elastic 104 in these trough-segments 104b may be kept as low as possible.

As will be apparent from FIGS. 9(a) and 9(b), the trough-segment 104b of the continuous elastic 104 left free hangs down under its own weight from the outer peripheral surface 109 of the rotary drum 108 as this trough-segment 104b moves to the lower region of the rotary drum 108. Referring to FIG. 9(a), the trough-segment 104b of the continuous elastic 104 conveyed by the outer peripheral surface of the rotary drum 108 is gradually displaced inward (as indicated by an arrow Q) to restore its initial rectilinear position. In the course of moving over the distance L from the station 200 to implement the step (D) to the station 201 to implement the step (D), the trough-segment 104b gradually moves toward the first side edge 106 and, in the second step or station 201, the trough-segment 104b substantially restores its initial rectilinear position immediately before being squeezed between the second pressure roll 105 and the rotary drum 108 (See FIG. 9(b)).

The trough-segment 104b is able to restore its initial rectilinear position in the course of being conveyed over the distance L without coming in contact with the first surface 102A of the first web 102. In other words, the trough-segment 104b is free from any contact resistance and can fully exert its contractile force without making any wrinkle of the first surface 102A of the first web 102 in the trough-segment 104b and without causing leakage of bodily fluids. This is preferable also from the standpoint of appearance.

Even if the trough-segment 104 itself exerts contractile force restoring force trying to move further inward, the auxiliary sheet 115 firmly fixed by dually coated adhesive serves as positioning means adapted to prevent the trough-segment 104b from further moving inward, i.e., toward the front waist region 13.

As the respective components of the disposable diaper 10 according to the present invention, the well known materials widely used in the relevant technical field may be used without limitation. Construction of the diaper 10 according to the present invention is not limited to the construction of the illustrated pant-type diaper so far as the diaper is formed by the composite web 122 comprising the continuous elastic 104 sandwiched and bonded between the first web 102 and the second web 105 serving as the materials for the rear section 21 and/or front section 20 of the outer member 11 so as to describe a predetermined curve. For example, it is possible without departing from the scope of the invention to attach a plurality of waist surrounding elastics along the peripheral edge of the waist-opening to extend in the transverse direction X of the diaper 10 or to arrange the elastics 23A, 23B associated with the front half peripheral edges of the respective leg-openings in the front section 20 in the same manner as the elastics 27 associated with the rear half peripheral edges of the respective leg-openings in the rear section 21.

The aspects of the present invention described above may be arranged in at least the following item(s):

(i) A method for making a disposable diaper which comprises a composite web (122) including a first web (102), a second web (105) laminated with and bonded to the first web and a continuous elastic (104) sandwiched and bonded between the first web and the second web in a curved pattern, wherein the first web has a first surface (102A), a second surface opposed to the first surface, a first side edge (106) extending in a machine direction (MD) and a second side edge (107) opposed to and spaced from the first side edge in a cross direction (CD) orthogonal to the machine direction, the method comprising steps of:

(A) coating the first surface of the first web with an adhesive (130) to define an adhesion region (131) extending from the first side edge toward the second side edge in the cross direction (CD) and a non-adhesion region (134) extending along the second side edge in the machine direction and having a width dimension W;

(B) rocking the continuous elastic by a rocker arm (113) in a direction intersecting the machine direction and thereby laying the continuous elastic on the first surface of the first web in the curved pattern such that the continuous elastic has crest-segments (104a) each curving convexly toward the first side edge, trough-segments (104b) each defined between a pair of adjacent the crest-segments and curving concavely from the first side edge and intermediate segments (104c) connecting the crest-segments to the trough-segments;

(C) attaching the continuous elastic by only said crest-segments and the intermediate segments to the first surface of the first web in the adhesion region by a first pressure roll (112); and (D) superimposing and bonding together the first web and the second web by a second pressure roll (118).

(vi) An apparatus for making a disposable diaper which comprising a composite web (122) including a first web (102), a second web (105) laminated with and bonded to the first web and a continuous elastic (104) sandwiched and bonded between the first web and the second web in a curved pattern, the apparatus being characterized in that:

the apparatus includes at least a rotary drum (108) adapted to carryout a step of attaching the continuous elastic to the first web and a pressure roll (112) provided in face-to-face relationship with the rotary drum;

the continuous elastic has segments attached to the first surface of the first web in an adhesion region coated with an adhesive (130) and segments left free in a non-adhesion region (134) of the first surface of the first web coated with no adhesive;

the pressure roll has a cylindrical shape having a smaller-diameter section on a side of one end in comparison to a section on a side of another end and adapted not to effect a press step; and the smaller-diameter section is kept spaced from and opposed to the regions of the continuous elastic lying in the non-adhesion region in a step during which the first web having the continuous elastic placed thereon is squeezed between the rotary drum and the pressure roll.

The aspect of the present invention described in the above items (i) and (vi) may provide one or more of the following advantageous effects:

(a) With such an arrangement, the first pressure roll has the smaller-diameter section on the side of one end in comparison to a section on the side of the other end and adapted to be not responsible for a press step and the smaller-diameter section is kept spaced from and opposed to the regions of the continuous elastic lying in the non-adhesion region in a step during which the first web having the continuous elastic placed thereon is squeezed between the rotary drum and the pressure roll. In other words, the trough-segments of the continuous elastic are not squeezed between the first pressure roll and the rotary drum and maintained free. This facilitates the trough-segments to restore the initial rectilinear positions. Even if the rocker arm rocks outward beyond the first web, the trough-segments of the continuous elastic reliably restore the initial rectilinear positions as has been described just above and therefore it is unnecessary for the first web to have an additional width dimension corresponding to the trough-segments before contraction thereof to the initial rectilinear positions. Thus waste of material can be reduced.

Additionally, one or more of the following embodiments are provided in accordance with further aspects:

(ii) The method further comprising a step of: (E) bonding a continuous auxiliary sheet (115) intersecting with the intermediate segments of the continuous elastic and extending in the machine direction to the first surface of the first web with an adhesive line coated on the surface of the continuous auxiliary sheet facing the first surface of the first web.

(iii) The continuous elastic and the continuous auxiliary sheet are substantially simultaneously attached by the first pressure roll to the first surface of the first web.

(iv) A distance from a third station to implement the step (C) to a fourth station to implement the step (D) is set to be larger than a distance defined between a first station to implement the step (A) and a second station to implement the step (B) as well as than a distance defined between the second station and the third station.

(v) Of the respective steps, at least the steps (C) and (D) are carried on a common rotary drum.

As used herein, the terms "first", "second", "third" and "fourth" are use merely for distinguishing between similar elements.

The invention claimed is:

1. A method for making a disposable diaper which comprises a composite web including a first web, a second web laminated with and bonded to said first web and a continuous elastic sandwiched and bonded between said first web and said second web in a curved pattern, wherein said first web has a first surface, a second surface opposed to said first surface, a first side edge extending in a machine direction and a second side edge opposed to and spaced from said first side edge in a cross direction orthogonal to said machine direction, said method comprising the steps of:

(A) coating said first surface of said first web with an adhesive to define an adhesion region extending from said first side edge toward said second side edge in said cross direction and a non-adhesion region extending along said second side edge in said machine direction;

(B) rocking said continuous elastic by a rocker arm in said cross direction and thereby laying said continuous elastic on said first surface of said first web in said curved pattern such that said continuous elastic has crest-segments each curving convexly toward said first side edge, trough-segments each defined between a pair of adjacent said crest-segments and curving concavely from said first side edge and intermediate segments connecting said crest-segments to said trough-segments;

(C) attaching said continuous elastic by only said crest-segments and said intermediate segments to said first surface of said first web in said adhesion region by a first pressure roll;

(D) superimposing and bonding together said first web and said second web by a second pressure roll; and (E) bonding a continuous auxiliary sheet intersecting with said intermediate segments of said continuous elastic and extending in said machine direction on said first surface of said first web with an adhesive line coated on the surface of said continuous auxiliary sheet facing said first surface of said first web.

2. The method defined by claim 1, wherein said continuous elastic and said continuous auxiliary sheet are substantially simultaneously attached by said first pressure roll to said first surface of said first web.

3. The method defined by claim 1, wherein a distance from a third station to implement said step (C) to a fourth station to implement said step (D) is set to be larger than a distance defined between a first station to implement said step (A) and a second station to implement said step (B) as well as than a distance defined between said second station and said third station.

4. The method defined by claim 1, wherein, of said respective steps, at least said steps (C) and (D) are carried a common rotary drum.

* * * * *